(12) United States Patent
Ci

(10) Patent No.: US 10,493,117 B2
(45) Date of Patent: Dec. 3, 2019

(54) CHINESE HERBAL ORAL PASTE FOR CONDITIONING ALLERGIC CONSTITUTION AND PROCESSING METHOD THEREOF

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 0 days.

(21) Appl. No.: 15/967,059

(22) Filed: Apr. 30, 2018

(65) Prior Publication Data

US 2019/0192596 A1    Jun. 27, 2019

(30) Foreign Application Priority Data

Dec. 26, 2017   (CN) .......................... 2017 1 1428986

(51) Int. Cl.
| | | |
|---|---|---|
| *A61K 36/00* | (2006.01) | |
| *A61K 36/238* | (2006.01) | |
| *A61K 36/605* | (2006.01) | |
| *A61K 36/752* | (2006.01) | |
| *A61K 36/484* | (2006.01) | |
| *A61K 36/736* | (2006.01) | |
| *A61K 35/64* | (2015.01) | |
| *A61K 35/586* | (2015.01) | |
| *A61K 36/28* | (2006.01) | |
| *A61K 47/26* | (2006.01) | |
| *A61K 9/00* | (2006.01) | |
| *A61K 45/06* | (2006.01) | |
| *A61P 37/08* | (2006.01) | |
| *A61K 36/481* | (2006.01) | |

(52) U.S. Cl.
CPC .......... *A61K 36/238* (2013.01); *A61K 9/0053* (2013.01); *A61K 35/586* (2013.01); *A61K 35/64* (2013.01); *A61K 36/28* (2013.01); *A61K 36/481* (2013.01); *A61K 36/484* (2013.01); *A61K 36/605* (2013.01); *A61K 36/736* (2013.01); *A61K 36/752* (2013.01); *A61K 45/06* (2013.01); *A61K 47/26* (2013.01); *A61P 37/08* (2018.01); *A61K 2236/13* (2013.01); *A61K 2236/51* (2013.01)

(58) Field of Classification Search
None
See application file for complete search history.

*Primary Examiner* — Qiuwen Mi
(74) *Attorney, Agent, or Firm* — Novick, Kim & Lee, PLLC; Allen Xue

(57) ABSTRACT

The present application discloses a Chinese herbal oral paste for conditioning allergic constitution. The Chinese herbal oral paste includes the following raw material components: divaricate saposhnikovia root, milkvetch root, largehead atractylodes rhizome, fructus tribuli, mulberry fruit, cicada slough, lightyellow sophora root, orange fruit, licorice, smoked plum, beautiful sweetgum fruit, glossy privet fruit, lilium brownii, cortex moutan, earthworm, villous amomum fruit, Chinese waxgourd peel, rice beans, India madder root, siegesbeckia herb, yerbadetajo herb, prepared fleeceflower root, arnebia root, tortoise-plastron gelatin, donkey-hide gelatin, and xylitol. The Chinese herbal oral paste of the present disclosure has a higher drug concentration and good taste, is particularly suitable for health preserving in winter and conditioning the allergic constitution, will not create negative effects or harm to the human body at all, and is capable of achieving certain efficacy of strengthening physical health.

20 Claims, 1 Drawing Sheet

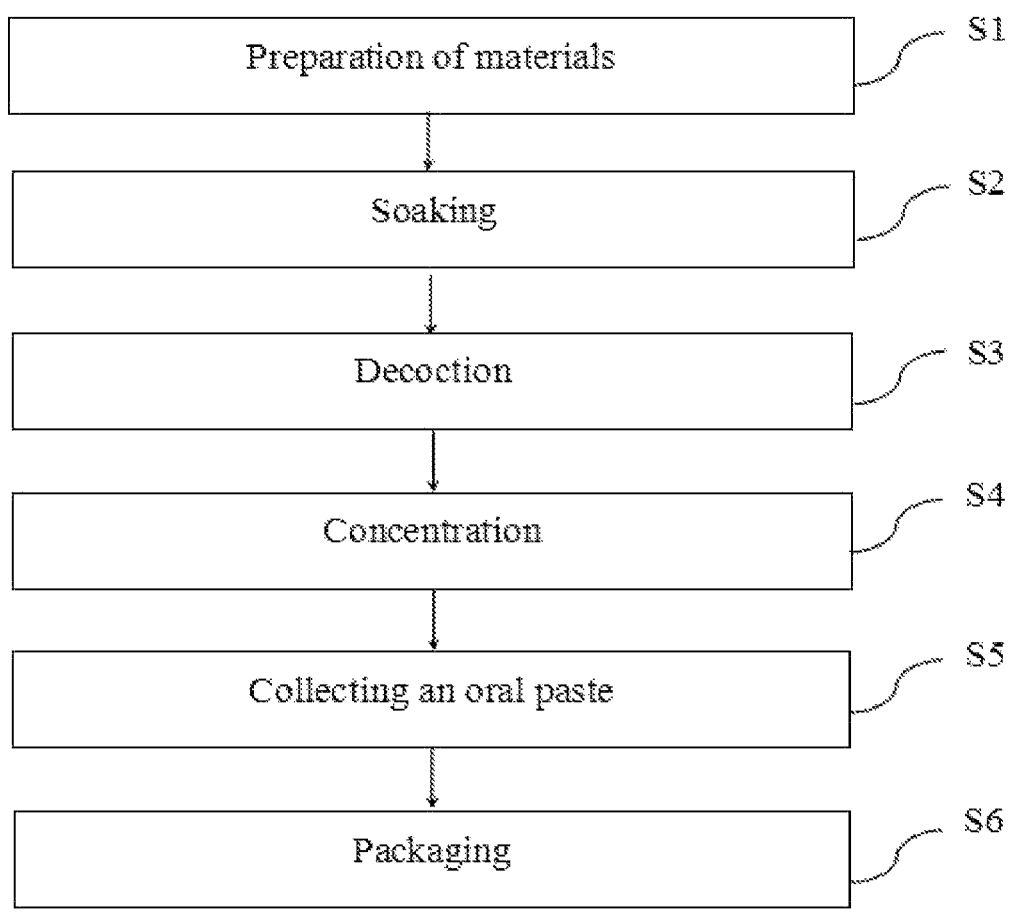

CHINESE HERBAL ORAL PASTE FOR CONDITIONING ALLERGIC CONSTITUTION AND PROCESSING METHOD THEREOF

TECHNICAL FIELD

The present disclosure relates to the field of health foods, and particularly to a Chinese herbal oral paste for conditioning allergic constitution and a processing method thereof.

BACKGROUND

In *Classification and Determination of Constitution in Traditional Chinese Medicine*, the China Association of Chinese Medicine classifies body constitutions of the human body into nine types, i.e., yin-yang harmony constitution, yang deficiency constitution, yin deficiency constitution, qi deficiency constitution, phlegm-dampness constitution, damp-heat constitution, qi depression constitution, blood stasis constitution, and allergic constitution, most of which are sub-healthy states.

The Allergic constitution is a special body constitution resulting from the factors such as congenital deficiencies and endowment heredity, including congenital or hereditary physiological defects, congenital or hereditary diseases, allergic reactions, primary immunodeficiency and the like. The general characteristic of the allergic constitution is congenital disorder, mainly characterized by physiological defects, allergic reactions and the like. People with allergic constitution generally have no other defects, but for people with abnormal native endowment, some may have malformations, and some may have physiological defects. The common manifestations are: people with allergic constitution usually suffer from asthma, wheal, throat itching, nasal obstruction, sneezing, etc.; people suffering from genetic diseases have the characteristics of vertical transmission, innateness, and being familial; and people with fetal-borne diseases have the characteristics of the mother's body affecting growth and development of fetus individuals and suffer from relevant diseases. People with allergic constitution have different psychological characteristics from each other, dependent on intrinsic nature. People with allergic constitution are susceptible to asthma, urticaria, pollinosis, drug allergies, etc. The allergic constitution is poor in adaptability to the external environment, for example, people with allergic constitution are poor in adaptability to the easy-to-sensitize season and are prone to chronic complaint.

Such sub-healthy constitution as allergic constitution belongs to chronic diseases and has a relatively long disease course, and requires a long-term medication and gradual conditioning, in order to achieve the effects of consolidating the vital essence and strengthening the origin, and strengthening the body resistance to eliminate pathogenic factors. The dosage forms commonly used in the traditional Chinese medicine are decoctions and Chinese patent medicine such as pills and the like. Decoctions usually have relatively good efficacy, but the administration thereof is complicated, and the taste thereof is poor, if the decoctions need to be administered for a long time, it is difficult for a patient to keep taking the decoctions. Moreover, the efficacy of the pills is relatively poor.

It is mentioned in the *Inner Canon of the Yellow Emperor* that "the superior physician prevents illness, the mediocre physician attends to impending illness, and the inferior physician treats actual illness", wherein the phrase "prevent illness" means taking corresponding measures to prevent the occurrence and development of diseases. The body constitution determines the health of people and determines the susceptibility to diseases. It is believed in the traditional Chinese medicine that since the human beings live in the natural world, physiological functions of the human body usually change with seasons, that is, "correspondence between man and nature". Winter is the season when the human body "stores energies", and appropriate nourishment can enhance the constitution, ward off diseases and strengthen the body, and prolong life, that is, conditioning in winter or nourishing in winter commonly mentioned in the traditional Chinese medicine. For the sub-healthy population with allergic constitution, to choose a solid oral paste with a higher drug concentration and good taste, and being convenient to carry is more adapted to requirements of modern people.

SUMMARY

A main object of the present disclosure is to provide a Chinese herbal nourishing product suitable for conditioning in winter so as to condition allergic constitution.

In order to achieve the above object, according to one aspect of the present disclosure, there is provided a Chinese herbal oral paste for conditioning allergic constitution.

The Chinese herbal oral paste for conditioning allergic constitution according to the present disclosure includes the following raw material components in parts by weight: 5-15 parts of divaricate saposhnikovia root, 10-20 parts of milkvetch root, 5-15 parts of largehead atractylodes rhizome, 13-27 parts of fructus tribuli, 15-27 parts of mulberry fruit, 4-13 parts of cicada slough, 5-16 parts of lightyellow sophora root, 6-19 parts of orange fruit, 3-8 parts of licorice, 7-18 parts of smoked plum, 9-22 parts of beautiful sweetgum fruit, 9-22 parts of glossy privet fruit, 20-40 parts of lilium brownii, 5-16 parts of cortex moutan, 5-16 parts of earthworm, 1-5 parts of villous amomum fruit, 13-30 parts of Chinese waxgourd peel, 5-17 parts of rice beans, 13-26 parts of India madder root, 12-27 parts of siegesbeckia herb, 14-28 parts of yerbadetajo herb, 20-40 parts of prepared fleeceflower root, 5-15 parts of arnebia root, 20-40 parts of tortoise-plastron gelatin, 5-15 parts of donkey-hide gelatin, and 15-35 parts of xylitol.

Furthermore, the Chinese herbal oral paste for conditioning allergic constitution according to the present disclosure includes the following raw material components in parts by weight: 7-13 parts of divaricate saposhnikovia root, 12-18 parts of milkvetch root, 7-13 parts of largehead atractylodes rhizome, 16-24 parts of fructus tribuli, 17-23 parts of mulberry fruit, 6-10 parts of cicada slough, 7-14 parts of lightyellow sophora root, 9-15 parts of orange fruit, 5-7 parts of licorice, 9-15 parts of smoked plum, 11-19 parts of beautiful sweetgum fruit, 11-19 parts of glossy privet fruit, 25-35 parts of lilium brownii, 7-13 parts of cortex moutan, 7-13 parts of earthworm, 2-4 parts of villous amomum fruit, 17-25 parts of Chinese waxgourd peel, 8-13 parts of rice beans, 17-22 parts of India madder root, 16-24 parts of siegesbeckia herb, 17-23 parts of yerbadetajo herb, 25-35 parts of prepared fleeceflower root, 7-12 parts of arnebia root, 25-35 parts of tortoise-plastron gelatin, 7-13 parts of donkey-hide gelatin, and 20-30 parts of xylitol.

Furthermore, the Chinese herbal oral paste for conditioning allergic constitution according to the present disclosure includes the following raw material components in parts by weight: 10 parts of divaricate saposhnikovia root, 15 parts of milkvetch root, 10 parts of largehead atractylodes rhizome, 20 parts of fructus tribuli, 20 parts of mulberry fruit, 8 parts of cicada slough, 10 parts of lightyellow sophora root, 12 parts of orange fruit, 6 parts of licorice, 12 parts of smoked plum, 15 parts of beautiful sweetgum fruit, 15 parts of glossy privet fruit, 30 parts of lilium brownii, 10 parts of cortex moutan, 10 parts of earthworm, 3 parts of villous amomum fruit, 20 parts of Chinese waxgourd peel, 10 parts of rice beans, 20 parts of India madder root, 20 parts of siegesbeckia herb, 20 parts of yerbadetajo herb, 30 parts of prepared fleeceflower root, 10 parts of arnebia root, 30 parts of tortoise-plastron gelatin, 10 parts of donkey-hide gelatin, and 25 parts of xylitol.

In order to achieve the above object, according to the other aspect of the present disclosure, there is provided a processing method for a Chinese herbal oral paste for conditioning allergic constitution.

The processing method for a Chinese herbal oral paste for conditioning allergic constitution according to the present disclosure includes the following steps in sequence: preparation of materials, soaking, decoction, concentration, and collecting an oral paste.

Furthermore, the step of preparation of materials is: measuring raw materials of formula amounts according to composition of the Chinese herbal oral paste, and cleaning raw materials, except tortoise-plastron gelatin, donkey-hide gelatin, and xylitol, for subsequent use.

Furthermore, the soaking step is: soaking the cleaned raw materials with 8-10 folds of water for 8-15 h, with the water over the raw materials by 10-20 cm.

Furthermore, the decoction step is: decocting the soaked drug materials over flame, firstly boiling the drug materials with high heat to sufficiently expand, then boiling the drug materials with low heat for 1-2 hours of decoction, then filtering the drug juice with gauze, then soaking filtered dregs of decoction with clear water and decocting the soaked dregs of decoction with low heat for 1 hour, repeated 2-4 times, combining the filtered drug juice, and squeezing and filtering the dregs to obtain a squeezed juice; combining decoction juice with the squeezed juice, followed by static settlement for 2 h, and filtering, to obtain a supernatant liquid for subsequent use.

Furthermore, the concentration step is: boiling and skimming the supernatant liquid resulted in the decoction step, followed by decoction concentration and stirring with gentle heat, until the drug liquid does not disperse when being dropped on paper, to obtain a vegetarian paste.

Furthermore, the step of collecting an oral paste is: pouring xylitol, and melted tortoise-plastron gelatin and donkey-hide gelatin into the vegetarian paste respectively, cooking them slowly with low heat, stirring them continuously with a shovel, until the juice coagulates into beads when dropped into clear water and does not disperse, and canning the resulted oral paste.

The melting step is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

The Chinese herbal oral paste of the present disclosure has a higher drug concentration and good taste, is particularly suitable for health preserving in winter and conditioning the allergic constitution, will not create negative effects or harm to the human body at all, and is capable of achieving certain efficacy of strengthening physical health.

BRIEF DESCRIPTION OF DRAWINGS

The accompanying drawing, which constitutes a part of the present application, is used to provide a further understanding of the present disclosure, so that other features, objects, and advantages of the present application become more obvious. The illustrative drawings for embodiments of the present disclosure and the description thereof are used to explain the present disclosure, rather than constitute an improper limitation on the present disclosure. In the drawing, FIG. 1 is a flow chart of a processing technology for a Chinese herbal oral paste of an embodiment of the present disclosure.

DETAILED DESCRIPTION OF EMBODIMENTS

In order to enable a person skilled in the art to better understand the solutions of the present application, the technical solutions of the embodiments of the present disclosure will be described clearly and completely below with reference to the accompanying drawing of the embodiments of the present application. Apparently, the embodiments described are merely for some of the embodiments of the present application, rather than all of the embodiments. All the other embodiments that are obtained by a person skilled in the art without inventive effort on the basis of the embodiments of the present application shall be covered by the protection scope of the present application.

In addition, the term "comprise" and any variant thereof are intended to cover non-exclusive inclusion, for example, a product comprising a series of raw materials or a method comprising a series of steps is not necessarily limited to the raw materials or the steps listed clearly, but can include other steps or raw materials that are not clearly listed or are inherent to the method and product.

It should be noted that the embodiments of the present application and the features of the embodiments can be combined with each other if there is no conflict. The present application will be described in detail below in combination with the embodiments.

The present disclosure provides a Chinese herbal oral paste for conditioning allergic constitution, including the following raw material components: divaricate saposhnikovia root, milkvetch root, largehead atractylodes rhizome, fructus tribuli, mulberry fruit, cicada slough, lightyellow sophora root, orange fruit, licorice, smoked plum, beautiful sweetgum fruit, glossy privet fruit, lilium brownii, cortex moutan, earthworm, villous amomum fruit, Chinese waxgourd peel, rice beans, India madder root, siegesbeckia herb, yerbadetajo herb, prepared fleeceflower root, arnebia root, tortoise-plastron gelatin, donkey-hide gelatin, and xylitol.

Divaricate saposhnikovia root is acrid and sweet in flavor and slightly warm in nature, acts on bladder, lung, spleen, and liver, dispels wind to relieve exterior syndrome, clears dampness to stop pain, arrests convulsion, and is used for exterior syndrome, rubella pruritus, arthralgia due to wind-dampness, tetanus symptom, and spleen-deficiency dampness.

Milkvetch root is sweet in flavor and slightly warm in nature, acts on lung, spleen, liver, and kidney, tonifies defensive-qi and secures the exterior, replenishes qi and invigorates yang, draws toxin and promotes tissue generation, alleviates water retention and relieves swelling, and is used for special lassitude, reduced appetite and loose stool, sinking of qi of middle energizer, rectocele due to chronic diarrhea, spontaneous perspiration and night sweating, blood-deficiency etiolation, dorsal furuncle borderless swelling, special edema, and internal-heat consumptive thirst.

Largehead atractylodes rhizome is bitter and sweet in flavor and warm in nature, acts on spleen and stomach, tonifies spleen and qi, dries dampness and alleviates water retention, constrains sweating, prevents miscarriage, and is used for reduced spleen-deficiency appetite, abdominal distension diarrhea, phlegm and fluid retention and palpitation, edema, spontaneous perspiration, and fetal upset.

Fructus tribuli is bitter, acrid, and neutral, acts on liver, calms liver and resolves depression, dispels wind and improves eyesight, and is used for hypertension vertigo and headache, liver depression and hypochondriac pain, headache due to pathogenic wind-heat, sore red swollen eyes, skin itch and other diseases.

Mulberry fruit is sweet and cold, acts on heart, liver, and kidney, nourishes yin and replenishes blood, moistens intestines, promotes the secretion of body fluid, and is used for yin-deletion blood depletion, yin-deficiency consumptive thirst, body fluid deletion thirst, vertigo and tinnitus, and constipation due to intestinal dryness.

Cicada slough is sweet and salty in flavor and cool in nature, acts on lung and liver, dispels wind and heat from the body, relieves sore throat and eases up the voice, promotes eruption, improves eyesight and removes nebula, calms endogenous wind to relieve spasm, and is used for wind-heat type common cold, onset of epidemic febrile disease, pharyngalgia and hoarseness, measles without adequate eruption, rubella pruritus, red eyes and nebula, acute and chronic infantile convulsion, tetanus symptom, and morbid night crying.

Lightyellow sophora root is bitter in flavor and cold in nature, acts on heart, liver, stomach, large intestine, and bladder, removes heat to dry dampness, kills helminth, promotes urination, and is used for heat-type dysentery, hematochezia, jaundice and anuresis, leukorrhea with reddish discharge, vulval swelling and vulval pruritus, eczema, skin itching, scab and leprosy, and is used for external treatment of trichomonas vaginitis.

Orange fruit is bitter, acrid, sour, and slightly cold, acts on spleen and stomach, regulates qi and the middle energizer, removes stagnation and flatulence, and is used for distending pain in chest and qi stagnation, distention and pain, indigestion, phlegm-fluid retention and congestion, and flagging of internal organs.

Licorice is sweet and neutral, acts on heart, lung, spleen, and stomach, supplements spleen and tonifies qi, removes heat and toxic matters, eliminates phlegm and relieves cough, relieves spasm and alleviates pain, moderates various drugs, and is used for weakness of spleen and stomach, lassitude and asthenia, palpitation and short of breath, cough with excessive phlegm, abdominal distention, four-limb spasm and pain, carbuncle, and alleviation of drug toxicity and intensity.

Smoked plum is sour and astringent in flavor and neutral in nature, acts on liver, spleen, lung, and large intestine, astringes lung and intestine, promotes the secretion of body fluid, calms ascaris, and is used for chronic cough caused by lung deficiency, prolonged diarrhea and dysentery, deficiency-heat consumptive thirst, ascaris-caused syncope, vomiting and abdominal pain.

Beautiful sweetgum fruit is bitter in flavor and neutral in nature, acts on liver and kidney, has the efficiacies of dispelling wind and activating collaterals, alleviating water retention, and invigorating menstrual flow, and is used for joint arthralgia, numbness and spasm, edema distention, hypogalactia, and amenorrhea.

Glossy privet fruit is sweet, bitter, and cool, acts on liver and kidney, nourishes liver and kidney, improves eyesight, removes asthenic fever, and is mainly used for treatment of dizziness, premature graying of hair, blurred vision, and fever due to yin deficiency.

Lilium brownii is sweet in flavor and cold in nature, acts on heart and lung, nourishes yin and moistens lung, clears away the heart fire and calms mind, and is used for yin-deficiency irritating dry cough, over-strained cough and hemoptysis, dysphoria and pavor, insomnia and dreamful sleep, and trance.

Cortex moutan is bitter and acrid in flavor and slightly cold in nature, acts on heart, liver, and stomach, removes heat to cool blood, invigorates blood circulation to remove blood stasis, eliminates steaming heat, and is used for blood-heat haematemesis, eruption, yin-deficiency internal heat, sweatless steaming bone, amenorrhea and algomenorrhea, traumatic injury, swelling pain of skin and external diseases, and intestinal carbuncle and abdominal pain.

Earthworm is salty and cold, acts on liver, spleen, and bladder, removes heat to calm endogenous wind, clears and activates channels and collaterals, clears lung to relieve asthma, removes heat to induce urination, and is used for high fever epilepsy, dementedness, arthralgia and paralysis of half body, lung-heat asthma, heat accumulation of bladder, difficult urination or anuresis.

Villous amomum fruit is acrid in flavor and warm in nature, acts on spleen, stomach, and kidney, promotes circulation of qi to regulate middle energizer, harmonizes stomach, refreshes spleen, and is used for treatment of abdominal pain and distension, anorexia and dyspepsia, dysphagia and vomiting, cold diarrhea and dysentery, and fetal movement.

Chinese waxgourd peel is sweet in flavor and cool in nature, acts on spleen and small intestine, promotes urination and relieves swelling, and is used for edema distention, difficult urination, summer-heat thirst, and scanty dark urine.

Rice beans are sweet and sour in flavor and neutral in nature, act on the heart and small intestine, alleviate water retention and relieve swelling, clear away toxic materials and discharge pus, and are used for edema distention, beriberi edema, jaundice and dark urine, wind-dampness pyretic arthralgia, carbuncle, and intestinal carbuncle and stomachache.

India madder root is bitter and cold, acts on liver, cools blood to stop bleeding, invigorates blood circulation to dispel stasis, and is used for hematemesis, bleeding from five sense organs or subcutaneous tissue, hematuria, hematochezia, amenorrhea due to stagnation of blood, traumatic pain, and arthralgia due to wind-dampness.

Siegesbeckia herb is bitter and cold, acts on liver and kidney, relieves rheumatism, strengthens muscles and bones, removes heat and toxic matters, and is used for arthralgia due to wind-dampness, numbness of limbs, carbuncle, and eczema pruritus.

Yerbadetajo herb is sweet and sour in flavor, cool in nature, and non-toxic, acts on liver and kidney, nourishes liver and kidney, cools blood to stop bleeding, and can be used for treatment of various diseases such as hematemesis, nasal hemorrhage, hemoptysis, intestinal hemorrhage, hematuria, hemorrhoidal bleeding, and metrorrhagia.

Prepared fleeceflower root is bitter, sweet, astringent, and slightly warm, acts on liver, heart, and kidney, nourishes liver and kidney, tonifies essence and blood, blackens hair and beard, strengthens muscles and bones, resolves turbidity and lowers lipid, and is used for blood-deficiency etiolation, vertigo and tinnitus, premature graying of hair, soreness and weakness of waist and knees, numbness of limb, metrorrhagia and leucorrhoea, and hyperlipemia.

Arnebia root is sweet, salty, and cold, acts on heart and liver, cools blood, invigorates blood, removes toxic matters and promotes eruption, and is used for blood-heat toxin, purple-black macula, measles without adequate eruption, skin and external diseases, eczema, burn due to hot liquid or fire, warm-heat macula, jaundice due to damp-heat, purpura, hematemesis, bleeding from five sense organs or subcutaneous tissue, hematuria, stranguria with turbid discharge, heat concentration constipation, burn, eczema, erysipelas, and large carbuncle.

Tortoise-plastron gelatin is sweet and salty in flavor and neutral in nature, nourishes yin, replenishes blood, stops bleeding, and is used for yin-deficiency blood depletion, consumptive heat and steaming bone, hematemesis, bleeding from five sense organs or subcutaneous tissue, dysphoria with smothery sensation and palpitation, kidney-deficiency backache, impotent feet and knees, metrorrhagia and metrostaxis, and leucorrhoea.

Donkey-hide gelatin is sweet in flavor and neutral in nature, acts on lung, liver, and kidney, replenishes blood and nourishes yin, moistens dryness, stops bleeding, and is used for blood-deficiency etiolation, vertigo and palpitation, dysphoria insomnia, and lung dryness cough.

Allergic constitution such as allergies is mainly inherited from parents, is incurred by epidemic pathogenic factor, has the manifestations of erythra, allergic rhinitis, or infertility. According to the constitution characteristics thereof, it is caused by qi-deficiency induced superficies unconsolidation, blood heat's facilitating onset of diseases caused by pathogenic wind, and inability of genetic endowment to endure epidemic pathogenic factor. The Chinese herbal oral paste of the present disclosure takes the general principle of invigorating qi for consolidating superficies, cooling blood and calming endogenous wind, and conditioning body. If superficial qi is consolidated, the body can resist pathogenic factors, and if blood and qi function normally, pathogenic wind is calmed. With the multiple types of drug materials of large dosages, efficacies of the various drug materials generate a synergistic effect, with the functions of replenishing lung qi, strengthening the body and being antiallergic, and the allergic constitution can be conditioned, so that people are vigorous with strong resistibility, and the occurrence of diseases is avoided. With the conditioning for such constitution, it is more targeted and will not create side effects, without harm to the human body at all, and can achieve certain efficacy of strengthening the body.

As shown in FIG. 1, the processing method for the Chinese herbal oral paste for conditioning allergic constitution of the present disclosure includes the following steps in sequence: preparation of materials, soaking, decoction, concentration, collecting an oral paste, and finally packaging. For specific operations of respective steps, reference can be made to various embodiments of the present disclosure.

EMBODIMENT 1

A Chinese herbal oral paste for conditioning allergic constitution includes the following raw material components in parts by weight: 15 parts of divaricate saposhnikovia root, 20 parts of milkvetch root, 15 parts of largehead atractylodes rhizome, 27 parts of fructus tribuli, 27 parts of mulberry fruit, 13 parts of cicada slough, 16 parts of lightyellow sophora root, 19 parts of orange fruit, 8 parts of licorice, 18 parts of smoked plum, 22 parts of beautiful sweetgum fruit, 22 parts of glossy privet fruit, 40 parts of lilium brownii, 16 parts of cortex moutan, 16 parts of earthworm, 1-5 parts of villous amomum fruit, 30 parts of Chinese waxgourd peel, 17 parts of rice beans, 26 parts of India madder root, 27 parts of siegesbeckia herb, 28 parts of yerbadetajo herb, 40 parts of prepared fleeceflower root, 15 parts of arnebia root, 40 parts of tortoise-plastron gelatin, 15 parts of donkey-hide gelatin, and 35 parts of xylitol.

The processing method thereof includes the following steps in sequence:

preparation of materials: measuring raw materials of formula amounts according to composition of the Chinese herbal oral paste, and cleaning raw materials, except tortoise-plastron gelatin, donkey-hide gelatin, and xylitol, for subsequent use;

soaking: soaking the cleaned raw materials with 8 folds of water for 8 h, with the water over the raw materials by 10 cm;

decoction: decocting the soaked drug materials over flame, firstly boiling the drug materials with high heat to sufficiently expand, then boiling the drug materials with low heat for 1 hour of decoction, then filtering the drug juice with gauze, then soaking filtered dregs of decoction with clear water and decocting the soaked dregs of decoction with low heat for 1 hour, repeated 4 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

EMBODIMENT 2

A Chinese herbal oral paste for conditioning allergic constitution includes the following raw material components in parts by weight: 5 parts of divaricate saposhnikovia root, 10 parts of milkvetch root, 5 parts of largehead atractylodes rhizome, 13 parts of fructus tribuli, 15 parts of mulberry fruit, 4 parts of cicada slough, 5 parts of lightyellow sophora root, 6 parts of orange fruit, 3 parts of licorice, 7 parts of smoked plum, 9 parts of beautiful sweetgum fruit, 9 parts of glossy privet fruit, 20 parts of lilium brownii, 5 parts of cortex moutan, 5 parts of earthworm, 1 parts of villous amomum fruit, 13 parts of Chinese waxgourd peel, 5 parts of rice beans, 13 parts of India madder root, 12 parts of siegesbeckia herb, 14 parts of yerbadetajo herb, 20 parts of prepared fleeceflower root, 5 parts of arnebia root, 20 parts of tortoise-plastron gelatin, 5 parts of donkey-hide gelatin, and 15 parts of xylitol.

The processing method thereof includes the following steps in sequence:

preparation of materials: measuring raw materials of formula amounts according to composition of the Chinese herbal oral paste, and cleaning raw materials, except tortoise-plastron gelatin, donkey-hide gelatin, and xylitol, for subsequent use;

soaking: soaking the cleaned raw materials with 10 folds of water for 15 h, with the water over the raw materials by 20 cm;

decoction: decocting the soaked drug materials over flame, firstly boiling the drug materials with high heat to sufficiently expand, then boiling the drug materials with low heat for 2 hours of decoction, then filtering the drug juice with gauze, then soaking filtered dregs of decoction with clear water and decocting the soaked dregs of decoction with low heat for 1 hour, repeated 2 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

EMBODIMENT 3

A Chinese herbal oral paste for conditioning allergic constitution includes the following raw material components in parts by weight: 7 parts of divaricate saposhnikovia root, 12 parts of milkvetch root, 7 parts of largehead atractylodes rhizome, 16 parts of fructus tribuli, 17 parts of mulberry fruit, 6 parts of cicada slough, 7 parts of lightyellow sophora root, 9 parts of orange fruit, 5 parts of licorice, 17 parts of smoked plum, 11 parts of beautiful sweetgum fruit, 11 parts of glossy privet fruit, 25 parts of lilium brownii, 7 parts of cortex moutan, 7 parts of earthworm, 2 parts of villous amomum fruit, 17 parts of Chinese waxgourd peel, 8 parts of rice beans, 17 parts of India madder root, 16 parts of siegesbeckia herb, 17 parts of yerbadetajo herb, 25 parts of prepared fleeceflower root, 7 parts of arnebia root, 25 parts of tortoise-plastron gelatin, 7 parts of donkey-hide gelatin, and 20 parts of xylitol.

The processing method thereof includes the following steps in sequence:

preparation of materials: measuring raw materials of formula amounts according to composition of the Chinese herbal oral paste, and cleaning raw materials, except tortoise-plastron gelatin, donkey-hide gelatin, and xylitol, for subsequent use;

soaking: soaking the cleaned raw materials with 9 folds of water for 10 h, with the water over the raw materials by 12 cm;

decoction: decocting the soaked drug materials over flame, firstly boiling the drug materials with high heat to sufficiently expand, then boiling the drug materials with low heat for 1.5 hours of decoction, then filtering the drug juice with gauze, then soaking filtered dregs of decoction with clear water and decocting the soaked dregs of decoction with low heat for 1 hour, repeated 3 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

EMBODIMENT 4

A Chinese herbal oral paste for conditioning allergic constitution includes the following raw material components in parts by weight: 13 parts of divaricate saposhnikovia root, 18 parts of milkvetch root, 13 parts of largehead atractylodes rhizome, 24 parts of fructus tribuli, 23 parts of mulberry fruit, 10 parts of cicada slough, 14 parts of lightyellow sophora root, 15 parts of orange fruit, 7 parts of licorice, 15 parts of smoked plum, 19 parts of beautiful sweetgum fruit, 19 parts of glossy privet fruit, 35 parts of lilium brownii, 13 parts of cortex moutan, 13 parts of earthworm, 4 parts of villous amomum fruit, 25 parts of Chinese waxgourd peel, 13 parts of rice beans, 22 parts of India madder root, 24 parts of siegesbeckia herb, 23 parts of yerbadetajo herb, 35 parts of prepared fleeceflower root, 12 parts of arnebia root, 35 parts of tortoise-plastron gelatin, 13 parts of donkey-hide gelatin, and 30 parts of xylitol.

The processing method thereof includes the following steps in sequence:

preparation of materials: measuring raw materials of formula amounts according to composition of the Chinese herbal oral paste, and cleaning raw materials, except tortoise-plastron gelatin, donkey-hide gelatin, and xylitol, for subsequent use;

soaking: soaking the cleaned raw materials with 9 folds of water for 12 h, with the water over the raw materials by 15 cm;

decoction: decocting the soaked drug materials over flame, firstly boiling the drug materials with high heat to sufficiently expand, then boiling the drug materials with low heat for 1.5 hours of decoction, then filtering the drug juice with gauze, then soaking filtered dregs of decoction with clear water and decocting the soaked dregs of decoction with low heat for 1 hour, repeated 3 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

EMBODIMENT 5

A Chinese herbal oral paste for conditioning allergic constitution includes the following raw material components in parts by weight: 10 parts of divaricate saposhnikovia root, 15 parts of milkvetch root, 10 parts of largehead atractylodes rhizome, 20 parts of fructus tribuli, 20 parts of mulberry fruit, 8 parts of cicada slough, 10 parts of lightyellow sophora root, 12 parts of orange fruit, 6 parts of licorice, 12 parts of smoked plum, 15 parts of beautiful sweetgum fruit, 15 parts of glossy privet fruit, 30 parts of lilium brownii, 10 parts of cortex moutan, 10 parts of earthworm, 3 parts of villous amomum fruit, 20 parts of Chinese waxgourd peel, 10 parts of rice beans, 20 parts of India madder root, 20 parts of siegesbeckia herb, 20 parts of yerbadetajo herb, 30 parts of prepared fleeceflower root, 10 parts of arnebia root, 30 parts of tortoise-plastron gelatin, 10 parts of donkey-hide gelatin, and 25 parts of xylitol.

The processing method thereof includes the following steps in sequence:

preparation of materials: measuring raw materials of formula amounts according to composition of the Chinese herbal oral paste, and cleaning raw materials, except tortoise-plastron gelatin, donkey-hide gelatin, and xylitol, for subsequent use;

soaking: soaking the cleaned raw materials with 9 folds of water for 13 h, with the water over the raw materials by 18 cm;

decoction: decocting the soaked drug materials over flame, firstly boiling the drug materials with high heat to sufficiently expand, then boiling the drug materials with low heat for 1.5 hours of decoction, then filtering the drug juice with gauze, then soaking filtered dregs of decoction with clear water and decocting the soaked dregs of decoction with low heat for 1 hour, repeated 3 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

Experiment Example 1: below is a test of effects of the Chinese herbal oral paste for conditioning allergic constitution prepared according to Embodiment 5 of the present disclosure.

Basic conditions of cases: 100 clinical cases of allergic constitution, including 50 male cases and 50 female cases. The youngest was aged 7, and the oldest was aged 64. 10 cases had allergic constitution, and often had nasal obstruction, sneezed, had a runny nose, even when they did not have a cold, and were susceptible to asthma; 15 cases easily got allergic to drugs and food; 10 cases were susceptible to smell and pollen allergies; 10 cases were prone to seasonal allergies; 25 cases were susceptible to skin urticaria, often had magenta spots and ecchymoses on the skin due to allergies, and once scratched, the skin often turned red with scratches; and 30 cases had other symptoms of allergic constitution.

Usage and dosage: 25 g each time, once a day. Brew 25 g of the oral paste with boiling water in a cup, and stir them to make the oral paste melt for administration.

Evaluation criteria for therapeutic effects:

Cured: clinical symptoms were completely eliminated, and normal life was restored.

Effective: clinical symptoms were partially eliminated, and various signs were gradually improved.

Ineffective: symptoms and signs were not obviously improved.

Result statistics: 57 cases cured, effective to 36 cases, and ineffective to 7 cases, i.e., effective to 93 cases in total, therefore the total effective rate was 93%.

It should be indicated that Embodiments 1-5 of the present invention are merely some of the embodiments for implementing the technical solutions of the present invention, and should not be construed as the scope of protection of the present invention merely limited to the above five embodiments, and a person skilled in the art can make further improvements on the basis of the present invention without departing from the principle and spirit of the present invention.

For example, the components of the Chinese herbal oral paste of the present invention are not limited to those listed in respective embodiments, while other Chinese herbal medicines also can be added, to further perfecting the drug formulation of the Chinese herbal oral paste of the present invention.

For another example, in the process of the processing method for the Chinese herbal oral paste of the present invention, in the concentration step, when the drug juice is concentrated to the vegetarian paste, a wild jujube shell powder is added evenly with stirring. The wild jujube shell powder above is obtained by sufficiently smashing and grinding the wild jujube shell, with a particle size of 100-400 micrometers. The wild jujube shell powder has the main components of cellulose and lignin, has quite advanced pores in the powder particles, and is a natural drug carrier. When added to the Chinese herbal oral paste, the pores inside the wild jujube shell powder will be filled up with the drug components of the Chinese herbal oral paste. Since the cellulose and lignin cannot be digested or absorbed in vivo, they can serve an effect of sustained release, and a small part of the drug components stored in the wild jujube shell powder can be released continuously, so that the drug is present in the digestive system for an extended period of time. The phenomenon that the drug components are wasted as the digestive system cannot absorb a large amount of drug components within a short period of time will not occur. The wild jujube shell powder is added in an amount of 1%-3% of the gelatin type drugs, and should not be used in an excessive amount, because the excessive amount, on one hand, will deteriorate the form quality of the oral paste, and on the other hand, will increase the burdens of the intestines and stomach as it cannot be absorbed by the human body.

The descriptions above are only preferred embodiments of the present invention, which are not used to limit the present invention. For a person skilled in the art, the present invention may have various changes and variations. Any modifications, equivalent substitutions, improvements etc. within the spirit and principle of the present invention shall all be included in the scope of protection of the present invention.

What is claimed is:

1. A Chinese herbal oral paste for conditioning allergic constitution, comprising the following raw material components in parts by weight: 5-15 parts of divaricate saposhnikovia root, 10-20 parts of milkvetch root, 5-15 parts of largehead atractylodes rhizome, 13-27 parts of fructus tribuli, 15-27 parts of mulberry fruit, 4-13 parts of cicada slough, 5-16 parts of lightyellow sophora root, 6-19 parts of orange fruit, 3-8 parts of licorice, 7-18 parts of smoked plum, 9-22 parts of beautiful sweetgum fruit, 9-22 parts of glossy privet fruit, 20-40 parts of lilium brownii, 5-16 parts of cortex moutan, 5-16 parts of earthworm, 1-5 parts of villous amomum fruit, 13-30 parts of Chinese waxgourd peel, 5-17 parts of rice beans, 13-26 parts of India madder root, 12-27 parts of siegesbeckia herb, 14-28 parts of yerbadetajo herb, 20-40 parts of prepared fleeceflower root, 5-15 parts of arnebia root, 20-40 parts of tortoise-plastron gelatin, 5-15 parts of donkey-hide gelatin, and 15-35 parts of xylitol.

2. The Chinese herbal oral paste for conditioning allergic constitution of claim 1, wherein the divaricate saposhnikovia root is 7-13 parts by weight, the milkvetch root is 12-18 parts by weight, the largehead atractylodes rhizome is 7-13 parts by weight, the fructus tribuli is 16-24 parts by weight, the mulberry fruit is 17-23 parts by weight, the cicada slough is 6-10 parts by weight, the lightyellow sophora root is 7-14 parts by weight, the orange fruit is 9-15 parts by weight, the licorice is 5-7 parts by weight, the smoked plum is 9-15 parts by weight, the beautiful sweetgum fruit is 11-19 parts by weight, the glossy privet fruit is 11-19 parts by weight, the lilium brownie is 25-35 parts by weight, the cortex moutan is 7-13 parts by weight, the earthworm is 7-13 parts by weight, the villous amomum fruit is 2-4 parts by weight, the Chinese waxgourd peel is 17-25 parts by weight, the rice beans is 8-13 parts by weight, the India madder root is 17-22 parts by weight, the siegesbeckia herb is 16-24 parts by weight, the yerbadetajo herb is 17-23 parts by weight, the prepared fleeceflower root is 25-35 parts by weight, the arnebia root is 7-12 parts by weight, the tortoise-plastron gelatin is 25-35 parts by weight, the donkey-hide gelatin is 7-13, and the xylitol is 20-30 parts by weight.

3. The Chinese herbal oral paste for conditioning allergic constitution of claim 1, wherein the divaricate saposhnikovia root is 10 parts by weight, the milkvetch root is 15 parts by weight, the largehead atractylodes rhizome is 10 parts by weight, the fructus tribuli is 20 parts by weight, the mulberry fruit is 20 parts by weight, the cicada slough is 8 parts by weight, the lightyellow sophora root is 10 parts by weight, the orange fruit is 12 parts by weight, the licorice is 6 parts by weight, the smoked plum is 12 parts by weight, the beautiful sweetgum fruit is 15 parts by weight, the glossy privet fruit is 15 parts by weight, the lilium brownie is 30 parts by weight, the cortex moutan is 10 parts by weight, the earthworm is 10 parts by weight, the villous amomum fruit is 3 parts by weight, the Chinese waxgourd peel is 20 parts by weight, the rice beans is 10 parts by weight, the India madder root is 20 parts by weight, the siegesbeckia herb is 20 parts by weight, the yerbadetajo herb is 20 parts by weight, the prepared fleeceflower root is 30 parts by weight, the arnebia root is 10 parts by weight, the tortoise-plastron gelatin is 30 parts by weight, the donkey-hide gelatin is 10, and the xylitol is 25 parts by weight.

4. A processing method for the Chinese herbal oral paste for conditioning allergic constitution of claim 1, comprising the following steps in sequence: preparation of materials, soaking, decoction, concentration, and collecting an oral paste.

5. The processing method for the Chinese herbal oral paste for conditioning allergic constitution of claim 4, wherein the step of preparation of materials is: measuring raw materials of formula amounts according to composition of the Chinese herbal oral paste, and cleaning raw materials, except tortoise-plastron gelatin, donkey-hide gelatin, and xylitol, for subsequent use.

6. The processing method for the Chinese herbal oral paste for conditioning allergic constitution of claim 5, wherein the soaking step is: soaking the cleaned raw materials with 8-10 folds of water for 8-15 h, with the water over the raw materials by 10-20 cm.

7. The processing method for the Chinese herbal oral paste for conditioning allergic constitution of claim 6, wherein the decoction step is: decocting the soaked drug materials over flame, firstly boiling the drug materials with high heat to sufficiently expand, then boiling the drug materials with low heat for 1-2 hours of decoction, then filtering the drug juice with gauze, then soaking filtered dregs of decoction with clear water and decocting the soaked dregs of decoction with low heat for 1 hour, repeated 2-4 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use.

8. The processing method for the Chinese herbal oral paste for conditioning allergic constitution of claim 7, wherein the concentration step is: boiling and skimming the supernatant liquid resulted in the decoction step, followed by decoction concentration and stirring with gentle heat, until a drug liquid does not disperse when being dropped on paper, to obtain a vegetarian paste.

9. The processing method for the Chinese herbal oral paste for conditioning allergic constitution of claim 8, wherein the step of collecting an oral paste is: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

10. The processing method for the Chinese herbal oral paste for conditioning allergic constitution of claim 9, wherein the melting step is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

11. A processing method for the Chinese herbal oral paste for conditioning allergic constitution of claim 2, comprising the following steps in sequence: preparation of materials, soaking, decoction, concentration, and collecting an oral paste.

12. The processing method for the Chinese herbal oral paste for conditioning allergic constitution of claim 11, wherein the step of preparation of materials is: measuring raw materials of formula amounts according to composition of the Chinese herbal oral paste, and cleaning raw materials, except tortoise-plastron gelatin, donkey-hide gelatin, and xylitol, for subsequent use.

13. The processing method for the Chinese herbal oral paste for conditioning allergic constitution of claim 12, wherein the soaking step is: soaking the cleaned raw materials with 8-10 folds of water for 8-15 h, with the water over the raw materials by 10-20 cm.

14. The processing method for the Chinese herbal oral paste for conditioning allergic constitution of claim 13, wherein the decoction step is: decocting the soaked drug materials over flame, firstly boiling the drug materials with high heat to sufficiently expand, then boiling the drug materials with low heat for 1-2 hours of decoction, then filtering the drug juice with gauze, then soaking filtered dregs of decoction with clear water and decocting the soaked dregs of decoction with low heat for 1 hour, repeated 2-4 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use.

15. The processing method for the Chinese herbal oral paste for conditioning allergic constitution of claim 14, wherein the concentration step is: boiling and skimming the supernatant liquid resulted in the decoction step, followed by decoction concentration and stirring with gentle heat, until a drug liquid does not disperse when being dropped on paper, to obtain a vegetarian paste.

16. The processing method for the Chinese herbal oral paste for conditioning allergic constitution of claim 15, wherein the step of collecting an oral paste is: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

17. The processing method for the Chinese herbal oral paste for conditioning allergic constitution of claim 16, wherein the melting step is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

18. A processing method for the Chinese herbal oral paste for conditioning allergic constitution of claim 3, comprising the following steps in sequence: preparation of materials, soaking, decoction, concentration, and collecting an oral paste.

19. The processing method for the Chinese herbal oral paste for conditioning allergic constitution of claim 18, wherein the step of preparation of materials is: measuring raw materials of formula amounts according to composition of the Chinese herbal oral paste, and cleaning raw materials, except tortoise-plastron gelatin, donkey-hide gelatin, and xylitol, for subsequent use.

20. The processing method for the Chinese herbal oral paste for conditioning allergic constitution of claim 19, wherein the soaking step is: soaking the cleaned raw materials with 8-10 folds of water for 8-15 h, with the water over the raw materials by 10-20 cm.

\* \* \* \* \*